US010188758B2

(12) United States Patent
Li et al.

(10) Patent No.: US 10,188,758 B2
(45) Date of Patent: Jan. 29, 2019

(54) ORGANIC COMPOUNDS

(71) Applicant: INTRA-CELLULAR THERAPIES, INC., New York, NY (US)

(72) Inventors: Peng Li, New Milford, NJ (US); Jun Zhao, Highland Park, NJ (US); Lawrence P. Wennogle, Hillsborough, NJ (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

(21) Appl. No.: 15/560,107

(22) PCT Filed: Mar. 18, 2016

(86) PCT No.: PCT/US2016/023198
§ 371 (c)(1),
(2) Date: Sep. 20, 2017

(87) PCT Pub. No.: WO2016/154027
PCT Pub. Date: Sep. 29, 2016

(65) Prior Publication Data
US 2018/0099060 A1   Apr. 12, 2018

Related U.S. Application Data

(60) Provisional application No. 62/135,915, filed on Mar. 20, 2015.

(51) Int. Cl.
*C07D 213/65* (2006.01)
*C07D 213/69* (2006.01)
*A61K 31/44* (2006.01)
*A61K 51/04* (2006.01)
*A61P 25/22* (2006.01)
*A61P 25/24* (2006.01)

(52) U.S. Cl.
CPC .......... *A61K 51/0455* (2013.01); *A61P 25/22* (2018.01); *A61P 25/24* (2018.01); *C07D 213/65* (2013.01); *C07D 213/69* (2013.01)

(58) Field of Classification Search
None
See application file for complete search history.

(56) References Cited

U.S. PATENT DOCUMENTS

| 8,183,266 B2 | 5/2012 | Wennogle et al. |
| 2009/0082597 A1 | 3/2009 | Grumann et al. |
| 2010/0120858 A1 | 5/2010 | Caprathe et al. |
| 2010/0267443 A1 | 10/2010 | Stangeland et al. |

FOREIGN PATENT DOCUMENTS

WO    WO-2008150528 A1 * 12/2008 ........... C07D 213/65

OTHER PUBLICATIONS

Amara et al., "Neurotransmitter Transporters: Recent Progress," Annu. Rev. Neurosci., 16: 73-93 (1993).
Axelrod et al., "The Uptake, Storage, Release and Metabolism of Noradrenaline in Sympathetic Nerves," Progress in Brain Research, 31: 21-32 (1969).
Benedetti et al., "Stereoselective and Species-Dependent Kinetics of Reboxetine in Mouse and Rat," Chirality, 7: 285-289 (1995).
Blakely et al., "Molecular Physiology of Norepinephrine and Serotonin Transporters," J. Exp. Biol., 196: 263-281 (1994).
Bonisch et al., "The Noradrenaline Transporter of the Neuronal Plasma Membrane," Ann. N.Y. Acad. Sci., 733: 193-202 (1994).
Charney et al., "Monoamine Dysfunction and the Pathophysiology and Treatment of Depression," J. Clin. Psychiatry, 59 (Suppl 14): 11-14 (1998).
Chumpradit et al., "Iodinated tomoxetine derivatives as selective ligands for serotonin and norepinephrine uptake sites," J. Med. Chem., 35(23): 4492-4497 (1992).
Ding et al., "Evaluation of a new norepinephrine transporter PET ligand in baboons, both in brain and peripheral organs," Synapse, 50(4): 345-352 (2003).
Frazer, "Antidepressants," J. Clin. Psychiatry, 58 (Suppl 6): 9-25 (1997).
Haka et al., "Synthesis and Regional Mouse Brain Distribution of [11C]Nisoxetine, a Norepinephrine Uptake Inhibitor," Nucl. Med. Biol., 16(8): 771-774 (1989).
International Search Report for International Application No. PCT/US2016/023198, dated Jun. 3, 2016, 3 pages.
Koch et al., "R-fluoxetine Increases Extracellular DA, NE, As Well As 5-HT in Rat Prefrontal Cortex and Hypothalamus: An in vivo Microdialysis and Receptor Binding Study," Neuropsychopharmacology, 27(6): 949-959 (2002).
Kung et al., "Characterization of [123I]IDAM as a novel single-photon emission tomography tracer for serotonin transporters," Eur. J. Nucl. Med., 26(8): 844-853 (1999).
Leonard, "The role of noradrenaline in depression: a review," J. Psychopharmacol., 11 (4 SUPPL): S39-47 (1997) (Abstract Only).
Moller, H.J., "Are All Antidepressants the Same?" J. Clin. Psychiatry, 61 (SUPPL 6): 24-28 (2000).
Mongeau et al., "The serotonergic and noradrenergic systems of the hippocampus: their interactions and the effects of antidepressant treatments," Brain Research Reviews, 23(3): 145-195 (1997).
Nelson, "A review of the efficacy of serotonergic and noradrenergic reuptake inhibitors for treatment of major depression," Biological Psychiatry, 46: 1301-1308 (1999).
Pacholczyk et al., "Expression cloning of a cocaine- and antidepressant-sensitive human noradrenaline transporter," Nature, 350: 350-354 (1991).
Ressler et al., "Role of norepinephrine in the pathophysiology and treatment of mood disorders," Biological Psychiatry, 46(9): 1219-1233 (1999).
Valentino, R.J., et al., "The locus coeruleus as a site for integrating corticotropin-releasing factor and noradrenergic mediation of stress responses," Ann. N.Y. Acad. Sci., 697: 171-187 (1993).

(Continued)

*Primary Examiner* — Zinna Northington Davis
(74) *Attorney, Agent, or Firm* — Hoxie & Associates LLC

(57) ABSTRACT

The present invention relates to novel pyridinoxy phenylpropanamines, their pharmaceutical compositions and methods of use. In addition, the present invention relates to therapeutic methods that penetrate the blood-brain barrier and regulate the norepinephrine and serotonin transporters ("NET/SERT").

19 Claims, 1 Drawing Sheet

(56) References Cited

OTHER PUBLICATIONS

Van Dort et al., "Synthesis of C-labeled desipramine and its metabolite 2-hydroxydesipramine: Potential radiotracers for pet studies of the norepinephrine transporter," Nuclear Medicine and Biology, 24(8): 707-711 (1997).

Wilson et al., "Synthesis and in vivo evaluation of novel radiotracers for the in vivo imaging of the norepinephrine transporter," Nuclear Medicine and Biology, 30: 85-92 (2003).

* cited by examiner

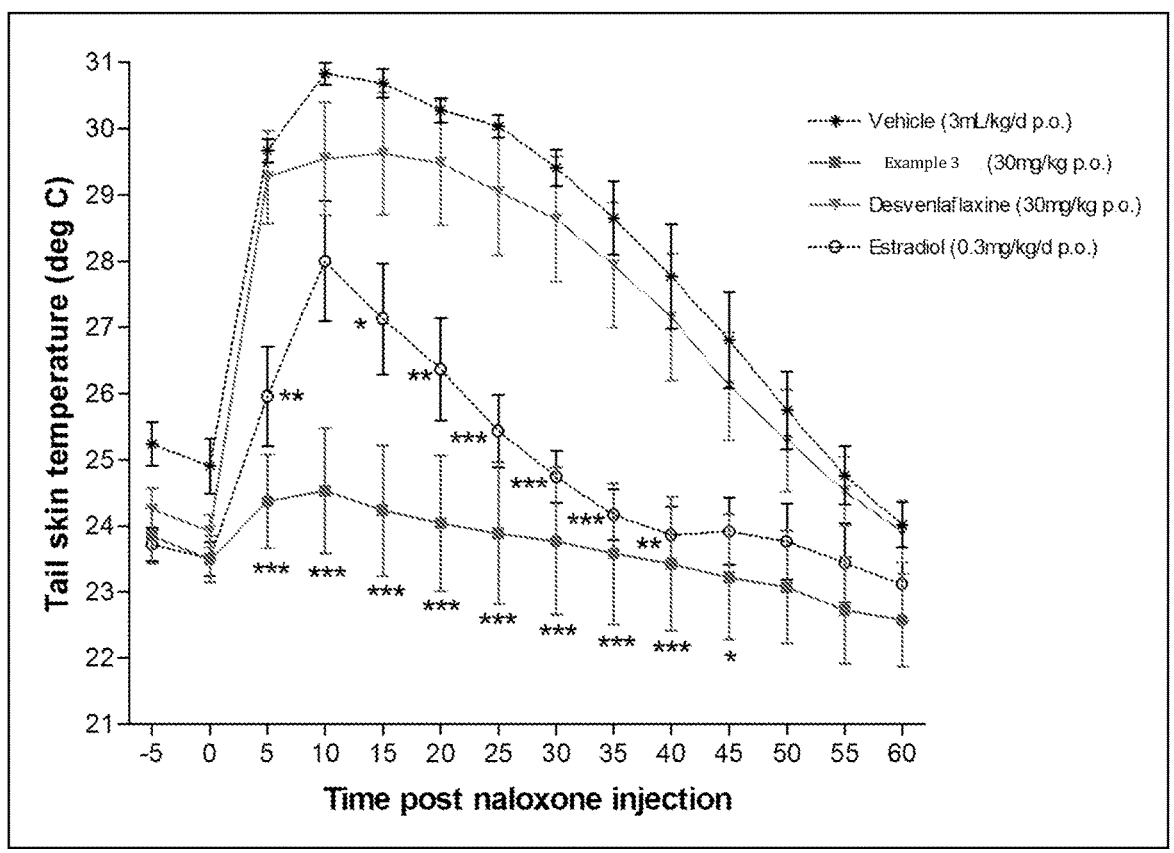

ORGANIC COMPOUNDS

CROSS REFERENCE TO RELATED APPLICATIONS

This application is a U.S. Application under 35 U.S.C. 371 claiming benefit of PCT Application No. PCT/US2016/023198, filed on Mar. 18, 2016, which claims priority to and the benefit of U.S. Provisional Application No. 62/135,915, filed on Mar. 20, 2015, the contents of each of which are hereby incorporated by reference in their entireties.

FIELD OF THE INVENTION

The present invention relates to novel 3-phenyl-3-pyridin-3-oxy propane-1-amine derivatives, their pharmaceutical compositions and methods of use. In addition, the present invention relates to therapeutic methods that penetrate the blood-brain barrier and regulate the norepinephrine and serotonin transporters ("NET/SERT"). Accordingly, the compounds and compositions of the present invention are useful in the treatment of depression, vasomotor symptoms, e.g., hot flashes and other diseases or conditions mediated by norepinephrine transporters ("NET") and/or serotonin transporters ("SERT"). The invention also relates to NET/SERT tracer compounds.

BACKGROUND OF THE INVENTION

Without being bound to theory, it is believed that norepinephrine transporter (NET), a 12 membrane spanning protein, located presynaptically on noradrenergic nerve terminals, plays a critical role in the regulation of the synaptic norepinephrine ("NE") concentration via the reuptake of NE (R. D. Blakely et al., *J. Exp. Biol*, 196:263-281(1994); T. Pacholczyk et al., *Nature*, 350:350-354(1994); and S. G. Amara et al., *Annu. Rev. Neurosci.*, 16:73-93(1993)). The NET is critical for the removal of NE from the extracellular space (J. Axelrod et al., Porg. *Brain Res.*, 31:21-32(1969); H. Bonisch at al., *Ann. Y. E Acad. Sci.*, 733: 193-202(1994)) and is a target for antidepressant drug actions (J. C. Nelso, *Psychiatry*, 46: 1301-1308(1999) and H. J. Moller, *J. Clin. Psychiatry*, 61 (SUPP.6):24-27(2000ï).

Many antidepressant drugs act by binding serotonin transporters ("SERT") and/or NET to increase serotonin and norepinephrine levels at neuronal synapses. While the role of SERTs in depression has long been explored, the NE system has also been proposed to be important in the treatment of depression. In the past, tricyclic antidepressant ("TCA") compounds and monoamine oxidase inhibitors ("MAOI") represented the major pharmacological treatments for this illness. Such drugs have the disadvantage of their low selectivity and interaction with several other types of receptors causing unwanted side effects (A J. Frazer, *J. Clin. Psychiatry*, 58(SUEPJL):9-25(1997)).

In an attempt to provide improved medications, selective serotonin reuptake inhibitors ("SSR₁") such as fluoxetine, nisoxetine, reboxetine, and their analogues (shown below) have been developed to treat depression.

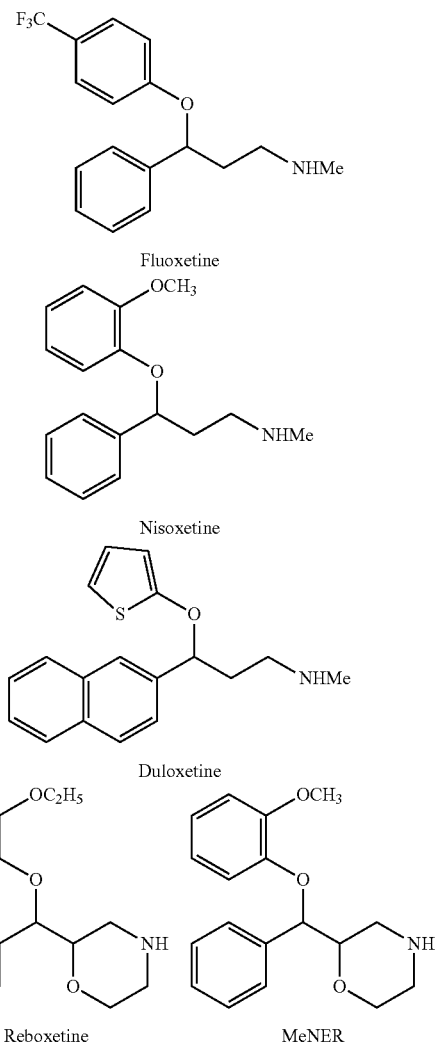

Some of these compounds are quite effective in certain patient populations. However, their use is often limited by side effects, particularly those thought to be mediated by their anticholinergic properties (R. Valentino et al., *Ann. N. Y. Acad. Sci.*, 697: 171-187(1993); R. Mongeau et al., *Brain Res. Rev.*, 23: 145-195(1997)). No simple increase or decrease in neuronal activity is likely to be the primary cause of depression. It may be that a complex dysregulation of the Locus Coeruleus-Norepinephrine system may play an important role in depression (K. J. Ressler et al., *Biol. Psychiatry*, 46: 1219-1233(1999)). Different studies had significant differences in NE metabolites and changes in receptor populations (D. Charney, *J. Clin. Psychiatry*, 59: 1 1-14(1998); B. Leonard, *J. Psychopharmacol.*, 11:s39-s47 (1997); A. Schatzberg et al., "Psychopharmacology: The Fourth Generation of Progress", pp. 911-920(1995)).

In addition to depression, the role of NET has also recently been implicated in thermoregulatory dysfunctions such as vasomotor symptoms, e.g., hot flashes experienced by naturally, chemically or surgically induced menopausal women. Although the physiology of hot flashes is still poorly understood today, studies have revealed an association of increased levels of norepinephrine in the preoptic hypothalamus in the brain to hot flashes. There is also supportive evidence for the role of norepinephrine (NE) and serotonin (5-HT) in thermoregulation. Compounds that modulate norepinephrine levels are therefore useful for the treatment of vasomotor symptoms.

The availability of new imaging tools such as selective positron emission tomography ("PET") and/or single photon emission computed tomography ("SPECT") radioligands for mapping specific transporter systems have significantly advanced the understanding of the field of depression and will be similarly useful in the understanding of other NET/SERT mediated disorders such as dysphoria, anxiety, sleep disorders, gastric motility disorders, sexual dysfunction, brain trauma, memory loss, appetite disorders, bulimia, obesity, substance abuse, alcoholism, tobacco addiction, obsessive-compulsive disease, panic disorder, premenstrual syndrome, migraine, bipolar disorders, neuropathic pain (e.g., chronic pain, e.g., fibromyalgia), attention deficit hyperactive disorder (ADHD), Alzheimer's Disease, and vasomotor symptoms, e.g., hot flashes, especially anxiety and depression. PET and SPECT make possible the direct study and quantification of neurotransmitter systems in the human brain and better understand psychiatric diseases. These target-specific radiotracers facilitate the development of therapeutic agents for depressive illness, optimize the therapeutic dosage, and monitor the efficacy of treatment. Despite recognition of the high importance of the NET as a site of action of many old (e.g. desipramine) and new (e.g. reboxetine) antidepressant drugs in the brain, and even though the NET has long been recognized in relation to the pathophysiology and treatment of ADHD, substance abuse, and depression, there have been relatively few attempts to develop radiotracers for imaging NET in vivo in the central nervous system ("CNS"), either by PET or SPECT (Wilson et al., *Nuclear Medicine and Biology*, 30:85-92(2003)).

Hake et al., *Nucl. Med. Biol.*, 16:771-574(1989) reported the synthesis of [$^{11}$C]nisoxetine as a PET ligand which demonstrated only modest specific binding in mice. Kung et al., *Eur. J. Nucl. Med. Molecular Imaging*, 26:844-853 (1999) synthesized an iodinated derivative of tomoxetine that showed a low degree of saturable binding in vivo in rat brain, and very high lung uptake. Chumpradit et al., *J. Med. Chem.*, 35:4492-4497(1992) and Koch et al., *Neuropsychopharmacology*, 27:949-959(2002) demonstrated in vitro that (R)-derivatives of fluoxetine had higher affinity to NE uptake sites than corresponding (S)-derivatives. Stolin et al., *Chirality*, 7:285-289(1995) showed that the (S, S) enantiomer of reboxetine is more potent than its (R,R) enantiomer ($IC_{50}$ 3.6 nM and 85 nM respectively) in inhibiting the NE uptake in rat hypothalamic synaptosomes. Ding et al., *Synapse*, 50:345-352(2003) reported an evaluation of the individual enantiomers of reboxetine methyl analog [$^{11}$C]MRB as radioligands for PET imaging studies of NET systems in baboons, both in brain and in peripheral organs. However, the results were not optimal due to high non-specific biding in vivo. The MRB tracer also displayed unexpected high uptake in striatum, a region that contains low levels of NET, and some binding to sites other than NET is suspected. Van Dort et al., *Nuclear Medicine and Biology*, 24:707-711(1997) has reported the radiosysnthesis of [$^{11}$C] desipramine but no in vivo data have been published yet.

There remains a need for a NET/SERT ligand with moderate lipophilicity and high binding affinity. Although the affinity of nisoxetine for NET is high, its lipophilicity is also undesirably high at log P>3.5.

SUMMARY OF THE INVENTION

In the first aspect, the disclosure provides a compound of formula (I):

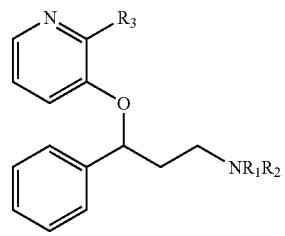

in free or salt form, wherein:
$R_1$ and $R_2$ are independently H or $C_{1-4}$ alkyl (e.g., methyl or ethyl); and
$R_3$ is n-$C_{2-4}$ alkyl (e.g., ethyl or n-propyl), or —O—$C_{1-4}$ alkyl (e.g., methoxy or ethoxy) optionally substituted hydroxy.

In a further embodiment of the first aspect, the compounds of the present disclosure are as follows:

1.1. Formula (I), wherein $R_1$ and $R_2$ are independently H or $C_{1-4}$ alkyl (e.g., methyl or ethyl);
1.2. Formula (I) or 1.1, wherein $R_1$ is hydrogen and $R_2$ is $C_{1-4}$ alkyl (e.g. methyl or ethyl);
1.3. Formula (I), 1.1 or 1.2, wherein $R_1$ is hydrogen and $R_2$ is ethyl;
1.4. Formula (I), 1.1 or 1.2, wherein $R_1$ is hydrogen and $R_2$ is methyl;
1.5. Formula (I) or 1.1, wherein $R_1$ and $R_2$ are both hydrogen;
1.6. Formula (I) or any of 1.1-1.5, wherein $R_3$ is n-$C_{2-4}$ alkyl (e.g., ethyl or n-propyl), or —O—$C_{1-4}$ alkyl optionally substituted hydroxy;
1.7. Formula (I) or any of 1.1-1.5, wherein $R_3$ is n-$C_{2-4}$ alkyl (e.g., ethyl or n-propyl), or —O—$C_{2-4}$ alkyl optionally substituted hydroxy
1.8. Formula (I) or any of 1.1-1.6, wherein $R_3$ is n-$C_{2-4}$ alkyl (e.g., ethyl or n-propyl);
1.9. Formula (I) or any of 1.1-1.6, wherein $R_3$ is ethyl;
1.10. Formula (I) or any of 1.1-1.6, wherein $R_3$ is n-propyl;
1.11. Formula (I) or any of 1.1-1.6, wherein $R_3$ is —O—$C_{1-4}$ alkyl (e.g. methoxy or ethoxy) optionally substituted with hydroxy;
1.12. Formula (I) or any of 1.1-1.6, wherein $R_3$ is —O—$C_{2-4}$ alkyl (e.g. ethoxy) optionally substituted with hydroxy;
1.13. Formula (I) or any of 1.1-1.6, wherein $R_3$ is —O—$C_{2-4}$ alkyl (e.g. methoxy or ethoxy);
1.14. Formula (I) or any of 1.1-1.6, wherein $R_3$ is methoxy;
1.15. Formula (I) or any of 1.1-1.6, wherein $R_3$ is ethoxy;
1.16. Formula (I) or any of 1.1-1.6, wherein $R_3$ is $C_{2-4}$ alkyl (e.g. ethyl) substituted with hydroxy;
1.17. Formula (I) or any of 1.1-1.6, wherein $R_3$ is hydroxy ethoxy;
1.18. Formula (I) or any of 1.1-1.6, wherein $R_3$ is 2-hydroxy ethoxy;
1.19. Formula (I) or any of 1.1-1.5, wherein $R_3$ is 2-hydroxy ethoxy, $R_1$ is hydrogen and $R_2$ is methyl;
1.20. Formula (I) or any of 1.1-1.5, wherein $R_3$ is ethoxy, and $R_1$ and $R_2$ are both hydrogen;
1.21. Formula (I) or any 1.1-1.20, wherein the chiral carbon bearing the oxy (—O—) group has an (R) absolute configuration;

1.22. Formula (I) or any 1.1-1.20, wherein the chiral carbon bearing the oxy (—O—) group has an (S) absolute configuration;
1.23. Formula (I) or any 1.1-1.20, wherein said compound is enantiomerically enriched with one enantiomer (e.g., wherein the absolute configuration of the chiral carbon bearing the oxy (—O—) group is predominantly (R) or predominantly (S)), for example, a compound having greater than 60% enantiomeric excess (ee), preferably greater than 75% ee, more preferably, greater than 85% ee, still more preferably, greater than 95% ee, most preferably great than 98% ee of one enantiomer;
1.24. Formula (I) or any 1.1-1.20, wherein said compound is enantiomerically enriched with the (R) enantiomer, e.g., a compound having greater than 60% ee, more preferably greater than 75% ee, still more preferably greater than 85% ee, still more preferably, greater than 95% ee, most preferably great than 98% ee of the (R) enantiomer;
1.25. Formula (I) or any 1.1-1.20, wherein said compound is enantiomerically enriched with the (S) enantiomer, e.g., a compound having greater than 60% ee, more preferably greater than 75% ee, still more preferably greater than 85% ee, still more preferably, greater than 95% ee, most preferably great than 98% ee of the (S) enantiomer;
1.26. Formula (I) or any 1.1-1.25, wherein said compound is selected from the group consisting of:

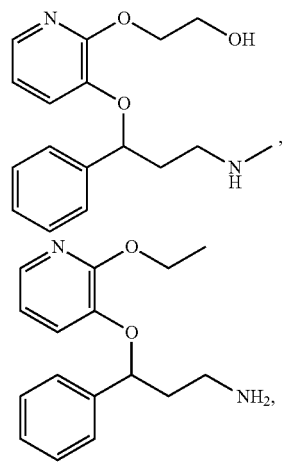

Example 3

Compound 4

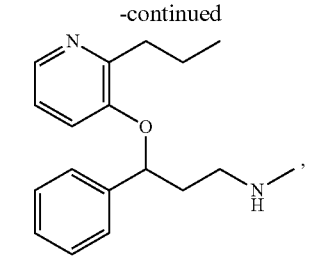

-continued

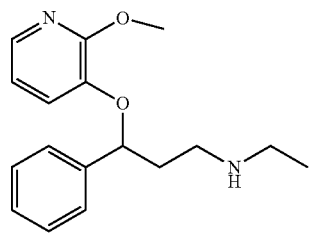

and

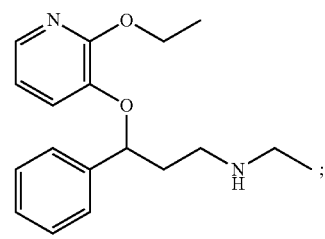

1.1. Formula (I) or any 1.1-1.25, wherein said compound is selected from the group consisting of:

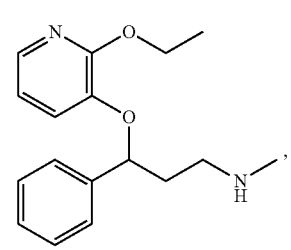

,

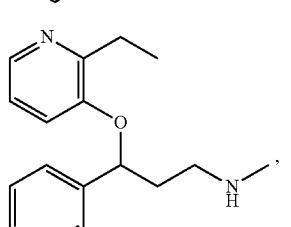

,

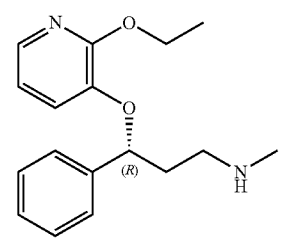

,

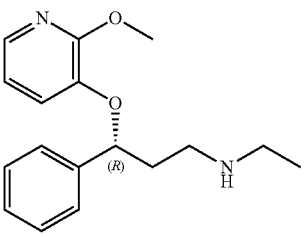

and

-continued

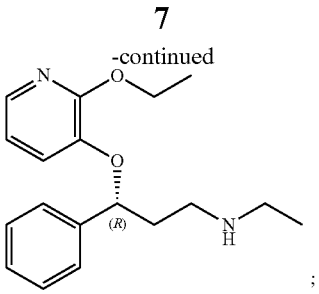

1.2. Any of the preceding formulae wherein said compounds have a $K_1$ of less than 10,000 nM, preferably less than 2,000 nM, still more preferably less than 100 nM, and most preferably less than 15 nM as described.

The inventors have found that the compounds defined in the present disclosure can penetrate the blood-brain barrier and regulate NET and/or SERT. Accordingly, the compounds of the present disclosure are useful in the treatment of NET/SERT mediated conditions, e.g., disease or condition characterized by dysfunctional regulation of NET/SERT, e.g., dysphoria, depression (including major depressive disorder, dysthymia, adjustment disorder with depressed mood, and depression associated with bipolar disorder), anxiety, sleep disorders, gastric motility disorders, sexual dysfunction, brain trauma, memory loss, appetite disorders, bulimia, obesity, substance abuse, alcoholism, tobacco addiction, obsessive-compulsive disease, panic disorder, premenstrual syndrome, migraine, bipolar disorders, neuropathic pain (e.g., chronic pain, e.g., fibromyalgia), attention deficit hyperactive disorder (ADHD), and naturally, surgically or medically-induced menopausal or andropausal symptoms such as vasomotor symptoms, e.g., hot flashes. In a preferred embodiment, the NET/SERT mediated condition is anxiety, depression or vasomotor symptoms.

Therefore, the compounds of the current disclosure are useful in the treatment, control and management of diseases characterized by the dysfunction or malregulation of NET/SERT, especially in the brain as described herein. Thus, there is provided a compound of the formula (I), e.g., any of formulae 1.1-1.2, in free or a pharmaceutically acceptable salt form, as defined hereinbefore for use as a medicament. In a further aspect of the present disclosure, there is provided a compound of the formula (I), e.g., any of formulae 1.1-1.2, in free or pharmaceutically acceptable salt thereof, for use in a method of treatment of the human or animal body by therapy, for example for use in a method of treatment, control and/or management of diseases characterized by the dysfunction or malregulation of NET/SERT, especially in the brain as described herein.

Therefore, in the second aspect, the disclosure provides a pharmaceutical composition which comprises a compound of the formula (I), e.g., any of formulae 1.1-1.2, in free or a pharmaceutically acceptable salt form, as defined hereinbefore, in association with a pharmaceutically-acceptable diluent or carrier.

In the third aspect, there is provided a method for producing a regulatory effect on NET in a warm-blooded animal, such as a man, in need of such NET/SERT regulating which comprises administering to said animal an effective amount of a compound of formula (I), e.g., any of formulae 1.1-1.2, in free or a pharmaceutically acceptable salt thereof.

In the fourth aspect, the disclosure provides a method of treating a disease or condition mediated by NET and/or SERT, e.g., a disease or condition characterized by dysfunctional regulation of NET/SERT, comprising administering an effective amount of a compound of formula (I), e.g., any of formulae 1.1-1.2, in free or pharmaceutically acceptable salt form, to a patient in need thereof. In a particular embodiment, the disclosure provides a method of treating a disease or condition mediated by NET and/or SERT as described herein, wherein said disease or condition is selected from: dysphoria, depression (including major depressive disorder, dysthymia, adjustment disorder with depressed mood, and depression associated with bipolar disorder), anxiety, sleep disorders, gastric motility disorders, sexual dysfunction, brain trauma, memory loss, appetite disorders, bulimia, obesity, substance abuse, alcoholism, tobacco addiction, obsessive-compulsive disease, panic disorder, premenstrual syndrome, migraine, bipolar disorders, neuropathic pain (e.g., chronic pain, e.g., fibromyalgia), attention deficit hyperactive disorder (ADHD), and naturally, surgically or medically-induced menopausal or andropausal symptoms such as vasomotor symptoms, e.g., hot flashes. In another particular embodiment, the disclosure provides a method of treating a disease or condition mediated by NET and/or SERT as described herein, wherein said disease or condition is anxiety or depression. In still another particular embodiment, the disclosure provides a method of treating a disease or condition mediated by NET and/or SERT as described herein, wherein said disease or condition is vasomotor symptoms, e.g., hot flashes. For example, the disclosure provides a method for treating, alleviating, preventing or controlling vasomotor symptoms, e.g., hot flashes, comprising administering to a subject in need thereof, a therapeutically effective amount of at least one compound of Formula (I), e.g., any of formulae 1.1-1.2, in free or pharmaceutically acceptable salt form as defined herein before and optionally in association with a pharmaceutically-acceptable diluent or carrier.

Recently, NET uptake inhibitors have been implicated in Alzheimer's Disease (AD). Postmortem data indicate that tau lesions in the locus coeruleus (LC), the primary source of subcortical norepinephrine (NE), may be the first identifiable pathology of AD. Recent data from basic research in animal models of AD indicate that loss of NE incites a neurotoxic proinflammatory condition, reduces Aβ clearance and negatively impacts cognition—recapitulating key aspects of AD. In addition, evidence linking NE deficiency to neuroinflammation in AD also exists. By promoting pro-inflammatory responses, suppressing anti-inflammatory responses and impairing Aβ degradation and clearance, LC degeneration and NE loss can be considered a triple threat to AD pathogenesis. Restoration of NE reverses these effects and slows neurodegeneration in animal models, raising the possibility that treatments which increase NE transmission may have the potential to delay or reverse AD-related pathology. Therefore, the compounds of the present disclosure are useful for the treatment of Alzheimer's Disease.

In another embodiment, the disclosure provides a method for treating, alleviating, preventing or controlling vasomotor symptoms comprising (a) administering to a subject in need thereof a therapeutically affective amount of a compound of Formula (I), e.g., any of formulae 1.1-1.2, in free or pharmaceutically acceptable salt form, as hereinbefore described, and (b) further administering sequentially or simultaneously, at least one other adrenergic$_{\alpha2}$ receptor antagonist.

According to the fifth aspect of the disclosure, there is provided the use of a compound of the formula (I), e.g., any of formulae 1.1-1.2, in free or a pharmaceutically acceptable salt thereof, as defined hereinbefore in the manufacture of a medicament for use in the regulation of NET/SERT in a warm-blooded animal such as man.

According to the sixth aspect of the disclosure, there is provided the use of a compound of the formula (I), e.g., any of formulae 1.1-1.2, in free or a pharmaceutically acceptable salt thereof, as defined hereinbefore in the manufacture of a medicament for use in the production of an NET/SERT regulator across the blood-brain barrier in a warm-blooded animal such as man.

According to the seventh aspect of the disclosure, there is provided the use of a compound of the formula (I), e.g., any of formulae 1.1-1.2, in free or salt form, as defined herein before in the manufacture of a medicament for use in the treatment of NET/SERT mediated conditions, e.g., a disease or condition characterized by dysfunctional regulation of NET/SERT, e.g., dysphoria, depression (including major depressive disorder, dysthymia, adjustment disorder with depressed mood, and depression associated with bipolar disorder), anxiety, sleep disorders, gastric motility disorders, sexual dysfunction, brain trauma, memory loss, appetite disorders, bulimia, obesity, substance abuse, alcoholism, tobacco addiction, obsessive-compulsive disease, panic disorder, premenstrual syndrome, migraine, bipolar disorders, neuropathic pain (e.g., chronic pain, e.g., fibromyalgia), attention deficit hyperactive disorder (ADHD), Alzheimer's Disease and naturally, surgically or medically-induced menopausal or andropausal symptoms such as vasomotor symptoms, e.g., hot flashes, especially anxiety, depression and vasomotor symptoms, e.g., hot flashes. In a preferred embodiment, the disclosure provides use of a compound of the formula (I), e.g., any of formulae 1.1-1.2, in free or a pharmaceutically acceptable salt form, in the manufacture of a medicament for the treatment of anxiety or depression. In another preferred embodiment, the disclosure provides use of a compound of the formula (I), e.g., any of formulae 1.1-1.2, in free or a pharmaceutically acceptable salt form, in the manufacture of a medicament for the treatment of any disease or condition characterized by naturally, surgically or medically-induced menopausal or andropausal symptoms such as vasomotor symptoms, e.g., hot flashes.

In the eighth aspect of the disclosure, there is provided a pharmaceutical composition which comprises a compound of the formula (I), e.g., any of formulae 1.1-1.2, in free or a pharmaceutically acceptable salt form, as defined herein before in association with a pharmaceutically-acceptable diluent or carrier for use in the treatment, control and management of diseases characterized by malregulation of NET/SERT. In a particular embodiment, the disclosure provides a pharmaceutical composition which comprises a compound of formula (I), e.g., any of formulae 1.1-1.2, in free or a pharmaceutically acceptable salt thereof, in admixture with a pharmaceutically acceptable diluent or carrier for use in the treatment, control and management of diseases characterized by malregulation of NET/SERT in the brain.

In a further aspect of the disclosure, there is provided a pharmaceutical composition which comprises a compound of the formula (I), e.g., any of formulae 1.1-1.2, in free or a pharmaceutically acceptable salt thereof, as defined herein before in association with a pharmaceutically-acceptable diluent or carrier for use in the treatment of NET/SERT mediated conditions, e.g., a disease or condition characterized by dysfunctional regulation of NET/SERT, e.g., dysphoria, depression (including major depressive disorder, dysthymia, adjustment disorder with depressed mood, and depression associated with bipolar disorder), anxiety, sleep disorders, gastric motility disorders, sexual dysfunction, brain trauma, memory loss, appetite disorders, bulimia, obesity, substance abuse, alcoholism, tobacco addiction, obsessive-compulsive disease, panic disorder, premenstrual syndrome, migraine, bipolar disorders, neuropathic pain (e.g., chronic pain, e.g., fibromyalgia), attention deficit hyperactive disorder (ADHD), Alzheimer's Disease and naturally, surgically or medically-induced menopausal or andropausal symptoms such as vasomotor symptoms, e.g., hot flashes, especially anxiety and depression and vasomotor symptoms, e.g., hot flashes.

In another aspect of the disclosure, there is provided a compound of the formula (I), e.g., any of formulae 1.1-1.2, in free or a pharmaceutically acceptable salt thereof, as defined herein before for use in the treatment of NET/SERT mediated conditions, e.g., a disease or condition characterized by dysfunctional regulation of NET/SERT, e.g., dysphoria, depression (including major depressive disorder, dysthymia, adjustment disorder with depressed mood, and depression associated with bipolar disorder), anxiety, sleep disorders, gastric motility disorders, sexual dysfunction, brain trauma, memory loss, appetite disorders, bulimia, obesity, substance abuse, alcoholism, tobacco addiction, obsessive-compulsive disease, panic disorder, premenstrual syndrome, migraine, bipolar disorders, neuropathic pain (e.g., chronic pain, e.g., fibromyalgia), attention deficit hyperactive disorder (ADHD), Alzheimer's Disease and naturally, surgically or medically-induced menopausal or andropausal symptoms such as vasomotor symptoms, e.g., hot flashes, especially anxiety and depression and vasomotor symptoms, e.g., hot flashes.

In addition to their use in therapeutic medicine, the compounds of formula (I), e.g., any of formulae 1.1-1.2, in free or pharmaceutically acceptable salt forms are also useful as pharmacological tools in the development and standardization of in vitro and in vivo test systems for the evaluation of the effects of regulation of NET and/or SERT, especially in the brain, as part of the search for new therapeutic agents. Therefore, in the ninth aspect, the disclosure provides NET/SERT tracer compounds useful for Gamma radiation-based imaging. Two commonly employed gamma radiation-based imaging techniques are Positron Emission Tomography (referred to as PET) and Single Photon Emission Computed Tomography (referred to as SPECT). Therefore, the tracer compounds of the current disclosure comprise (i) a NET/SERT inhibitor of the current disclosure as hereinbefore described, e.g., a compound of formula (I) or any of formulae 1.1-1.2, in free or pharmaceutically acceptable salt form; and (ii) a radionuclide chemically bound to said NET/SERT inhibitor. Examples of isotopes useful in gamma radiation-based imaging include Carbon-11 (referred to as 11C or C11), Fluorine-18 (referred to as 18F or F18), Technetium-99m (referred to as 99mTc or Tc99m), Indium-111 (referred to as 111In or In111) and Iodine-123 (referred to as 123I or I123).

Therefore, in a further embodiment of the ninth aspect, the radionuclide of the NET/SERT tracer compound of the current disclosure is selected from Carbon-11 (referred to as $^{11}C$ or $C^{11}$), Fluorine-18 (referred to as $^{18}F$ or $F^{18}$), Technetium-99m (referred to as $^{99}mTc$ or $Tc^{99}m$), Indium-111 (referred to as $^{111}In$ or $In^{111}$) and Iodine-123 (referred to as $^{123}I$ or $I^{123}$) preferably $^{11}C$ or $^{18}F$. For example, the NET/SERT tracer compound of the disclosure is the compound of Formula I or any of formulae 1.1-1.2, selected from any of the following:

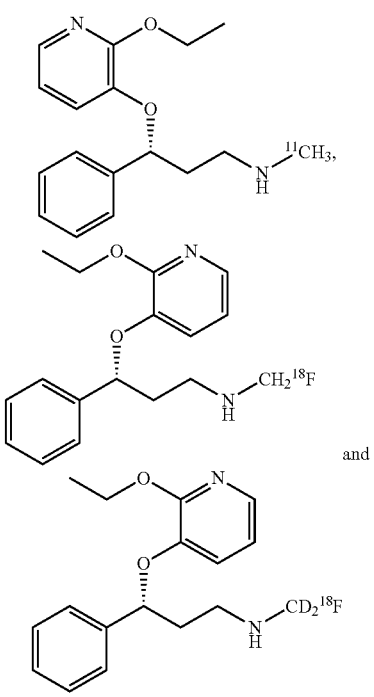

in free or pharmaceutically acceptable salt form.

BRIEF DESCRIPTION OF THE DRAWINGS

FIG. 1 shows the compound of Example 3 to be effective in reducing naloxone-inducted flush.

DETAILED DESCRIPTION OF THE DISCLOSURE

As used herein, the abbreviations in the specification are as follows:
"NE" refers to norepinephrine
"NET" refers to norepinephrine transporter(s).
"SERT" refers to serotonin transporter(s).
"NET/SERT" refers to norepinephrine and/or serotonin transporters.
"NRI/SRI" refers to norepinephrine/serotonin reuptake inhibitors.
"TCA" refers to tricyclic antidepressant(s).
"MAOI" refers to monoamine oxidase inhibitor(s).
"SSRI" refers to selective serotonin reuptake inhibitor(s).
"5-HT" refers to serotonin. "VMS" refers to vasomotor symptoms.
"PET" refers to positron emission tomography.
"SPECT" refers to photon emission computed tomography.
"ee" refers to enantiomeric excess.

The term "alkyl" includes both straight and branched chain alkyl groups. References to individual alkyl groups such as "propyl" are specific for the straight chain version only and references to individual branched chain alkyl groups such as 'isopropyl' are specific for the branched chain version only. For example, "$C_{1-4}$alkyl" includes $C_{1-4}$alkyl, $C_{1-3}$alkyl, propyl, isopropyl and isobutyl. The term "n-$C_{2-4}$ alkyl" is intended to be straight chain alkyl only, for example, n-propyl or n-butyl.

Where optional substituents are chosen from, for example, "1-5 independent" substituents from a list of substituents, it is to be understood that this definition includes all substituents being chosen from one of the specified groups or the substituents being chosen from two or more of the specified groups in the list. Where a substituent is recited using the molecule (parent) name, it is understood that the substituent is the radical of such molecular parent.

A salt of a compound of the disclosure is, for example, an acid-addition salt of a compound of the disclosure which is sufficiently basic, for example, an acid-addition salt with, for example, an inorganic or organic acid, for example hydrochloric, hydrobromic, sulphuric, phosphoric, trifluoroacetic, citric or maleic acid which affords a physiologically-acceptable cation, for example a salt with methylamine, dimethylamine, trimethylamine, piperidine, morpholine or tris-(2-hydroxyethyl)amine. In addition, a salt of a compound of the disclosure which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine. The Compounds of the Disclosure are intended for use as pharmaceuticals, therefore pharmaceutically acceptable salts are preferred. Salts which are unsuitable for pharmaceutical uses may be useful, for example, for the isolation or purification of free Compounds of the Disclosure, are therefore also included. Consequently, the present disclosure encompasses novel compounds of formula (I) in free or salt form, including salts that are suitable as well as salts which are unsuitable for pharmaceutical.

It is also to be understood that certain compounds of the formula (I) can exist in solvated as well as unsolvated forms such as, for example, hydrated forms. It is to be understood that the disclosure encompasses all such solvated forms which possess NET regulatory activity.

Further, it is understood that the compounds of formula (I) can exist in various stereoisomeric forms and in mixtures of such forms. The present disclosure encompasses all such forms and mixtures of such forms, enantiomers and chiral. The term "enantiomeric", "enantiomerically enriched" or "enantiomerically pure" form as used in this disclosure means substantially enriched with one enantiomer, wherein the absolute configuration of the chiral carbon bearing the oxy (—O—) group is predominantly (R) or predominantly (S), for example, a compound having greater than 60% enantiomeric excess (ee), preferably greater than 75% ee, more preferably, greater than 85% ee, still more preferably, greater than 95% ee, most preferably great than 98% ee of either the (R) or the (S) enantiomer. The term "enantiomeric excess" is a well known term and may be determined by one skilled in the art.

The chiral carbon bearing the oxy (—O—) group having an (R) or (S) absolute configuration refers to the following configurations:

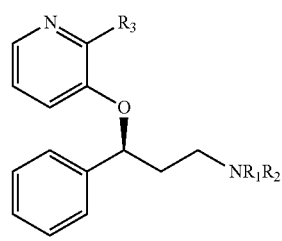

or

-continued

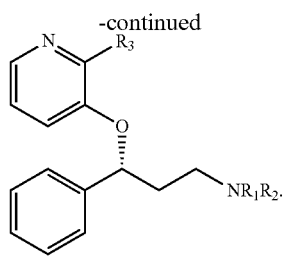

Particular values of variable groups are as defined herein. Such values may be used where appropriate with any of the definitions, claims or embodiments defined hereinbefore or hereinafter. In a preferred embodiment, the Compounds of Formula (I) are enriched with the (R) enantiomer in free or salt form.

It is intended that the compounds of the disclosure encompass their stable isotopes. For example, the hydrogen atom at a certain position on the compounds of the disclosure may be replaced with deuterium. It is expected that the activity of compounds comprising such isotopes would be retained and/or it may have altered pharmacokinetic or pharmacodynamic properties. In addition to therapeutic use, compounds comprising such isotopes and having altered pharmacokinetic or pharmacodynamic properties would also have utility for measuring pharmacokinetics of the non-isotopic analogs.

It is also intended that the compounds of the disclosure encompass compounds having chemically bound radionuclide such as those selected from Carbon-11 (referred to as $^{11}C$ or $C^{11}$), Fluorine-18 (referred to as $^{18}F$ or $F^{18}$), Technetium-99m (referred to as $^{99}mTc$ or $Tc^{99}m$), Indium-111 (referred to as $^{111}In$ or $In^{111}$) and Iodine-123 (referred to as $^{123}I$ or $I^{123}$) preferably $^{11}C$ or $^{18}F$ for use as, e.g., PET or SPECT tracer compounds as described in the ninth aspect of the current disclosure.

According to a further aspect of the disclosure, there is provided a pharmaceutical composition which comprises a compound of the formula (I), e.g., any of formulae 1.1-1.2, in free or a pharmaceutically acceptable salt form, as defined hereinbefore, in association with a pharmaceutically-acceptable diluent or carrier. The composition may be in a form suitable for oral administration, for example as a tablet or capsule, for parenteral injection (including intravenous, subcutaneous, intramuscular, intravascular, intradermal or infusion) as a sterile solution, suspension or emulsion, for topical administration as an ointment or cream or transdermal patches, or for rectal administration as a suppository.

In general, the above compositions may be prepared in a conventional manner using conventional excipients. The compound of formula (I) e.g., any of formulae 1.1-1.2, in free or salt form will normally be administered to a warm-blooded animal at a unit dose within the range 1-1000 mg/kg, and this normally provides a therapeutically effective dose. Preferably a daily dose in the range of 5-100 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present disclosure, there is provided a compound of the formula (I), e.g., any of formulae 1.1-1.2, in free or pharmaceutically acceptable salt thereof, for use in a method of treatment of the human or animal body by therapy.

NET/SERT mediated conditions include, but not limited to dysphoria, depression (including major depressive disorder, dysthymia, adjustment disorder with depressed mood, and depression associated with bipolar disorder), anxiety, sleep disorders, gastric motility disorders, sexual dysfunction, brain trauma, memory loss, appetite disorders, bulimia, obesity, substance abuse, alcoholism, tobacco addiction, obsessive-compulsive disease, panic disorder, premenstrual syndrome, migraine, bipolar disorders, neuropathic pain (e.g., chronic pain, e.g., fibromyalgia), attention deficit hyperactive disorder (ADHD), and naturally, surgically or medically-induced menopausal or andropausal symptoms such as vasomotor symptoms, e.g., hot flashes.

Recently, NET uptake inhibitors have been implicated in Alzheimer's Disease (AD). Postmortem data indicate that tau lesions in the locus coeruleus (LC), the primary source of subcortical norepinephrine (NE), may be the first identifiable pathology of AD. Recent data from basic research in animal models of AD indicate that loss of NE incites a neurotoxic proinflammatory condition, reduces Aβ clearance and negatively impacts cognition—recapitulating key aspects of AD. In addition, evidence linking NE deficiency to neuroinflammation in AD also exists. By promoting pro-inflammatory responses, suppressing anti-inflammatory responses and impairing Aβ degradation and clearance, LC degeneration and NE loss can be considered a triple threat to AD pathogenesis. Restoration of NE reverses these effects and slows neurodegeneration in animal models, raising the possibility that treatments which increase NE transmission may have the potential to delay or reverse AD-related pathology. Therefore, in a particular embodiment, the NET/SERT mediated disorder is Alzheimer's Disease.

The treatment methods include administering the compounds of the present disclosure, in free or pharmaceutically acceptable salt form, alone or together with other therapeutic compounds to treat NET/SERT mediated conditions as hereinbefore described, e.g., depression. Conjoint treatment may be achieved by way of the simultaneous, sequential or separate dosing of the individual components of the treatment. Such combination products employ the compounds of this disclosure within the dosage range described hereinbefore and the other pharmaceutically- active agent within its approved dosage range.

According to a further feature of the disclosure, there is provided a method for treating, alleviating, preventing or controlling vasomotor symptoms, e.g., hot flashes, comprising administering to a subject in need thereof, a therapeutically effective amount of at least one compound of Formula (I), e.g., any of formulae 1.1-1.2, in free or pharmaceutically acceptable salt form as defined herein before and optionally in association with a pharmaceutically-acceptable diluent or carrier.

The term "vasomotor symptoms" include, but are not limited to hot flashes (flushes), insomnia, sleep disturbances, mood disorders, irritability, excessive perspiration, night sweats, fatigue and other similar symptoms caused by thermoregulatory dysfunction. The term "hot flash" refers to an episodic disturbance of the body temperature leading to symptoms ranging from a warming sensation, intense heat on the upper body and face, redness, perspiration and sometimes followed by chills.

The treatment methods for vasomotor symptoms include administering the compounds of the present disclosure, in free or pharmaceutically acceptable salt form, e.g., Compound of Formula (I) or any of formulae 1.1-1.2, in free or pharmaceutically acceptable salt form, together with other therapeutic compounds to treat NET/SERT mediated conditions as hereinbefore described. Such conjoint treatment may be achieved by way of the simultaneous, sequential or separate dosing of the individual components of the treatment. Such combination products employ the compounds of this disclosure within the dosage range described hereinbefore and the other pharmaceutically-active agent within its approved dosage range.

A "therapeutically effective amount" refers to an amount of compounds (e.g., Compounds of Formula (I)) or compositions at specific dosages and for a specific amount of time, sufficient to treat a disease or condition, e.g., NET/SERT mediated conditions, e.g., a disease or condition characterized by dysfunctional regulation of NET/SERT, e.g., dysphoria, depression (including major depressive disorder, dysthymia, adjustment disorder with depressed mood, and depression associated with bipolar disorder), anxiety, sleep disorders, gastric motility disorders, sexual dysfunction, brain trauma, memory loss, appetite disorders, bulimia, obesity, substance abuse, alcoholism, tobacco addiction, obsessive-compulsive disease, panic disorder, premenstrual syndrome, migraine, bipolar disorders, neuropathic pain (e.g., chronic pain, e.g., fibromyalgia), attention deficit hyperactive disorder (ADHD), Alzheimer's Disease and naturally, surgically or medically-induced menopausal or andropausal symptoms such as vasomotor symptoms, e.g., hot flashes especially anxiety, depression and vasomotor symptoms, e.g., hot flashes. Wherein the therapeutic effective amount refers to a weight amount of the compounds of the disclosure, the weight amount is based on the compounds in free base form unless otherwise indicated.

The adrenergic$_{\alpha 2}$ receptor antagonists useful for the present disclosure include, but not limited to, atipamezole, 2-[2-(4-(2-methoxyphenyl)piperazin-1-yl)ethyl]-4,4-dimethyl-1,3-(2H, 4H)-isoquinolindione dihydrochloride (ARC 239 dihydrochloride), 2-[(4,5-dihydro-1H-imidazol-2-yl)methyl]-2,3-dihydro-1-methyl-1H-isoindole maleate (BRL 44408 maleat), BRL48962, BRL41992, SKF 104856, SKF 104078, MK912, 2-(2-ethyl-2,3-dihydro-2-benzofuranyl)-4,5-dihydro-1H-imidazole hydrochloride (efaroxan hydrochloride), 2-(1,4-benzodioxan-2-yl)-2-imidazoline hydrochloride (idazoxan hydrochloride), 2-(1-ethyl-2-indazoyl)methyl-1,4-benzodioxan hydrochloride (imiloxan hydrochloride), 17α-hydroxy-20α-yohimban-16B-carboxylic acid, methyl ester hydrochloride (rauwolscine hydrochloride), (8aR, 12aS, 13aS)-5,8, 8a, 9,10, 1 1,12, 12a, 13, 13a-dechydro-3-methoxy-12-(ethylsulfonyl)-6H-isoquino[2,1-y][1,6]naphthyridine hydrochloride (RS 79948 hydrochloride), 2-(2,3-dihydro-2-methoxy-1,4-benzodioxin-2-yl)-4,5-dihydro-1H-imidazole hydrochloride (RX 821002 hydrochloride), 8-[(2,3-dihydro-1,4-benzodioxin-2-yl)methyl]-1-phenyl-1,3,8-triazaspiro[4,5]decan-4-one (spiroxatrine), 17a-hydroxyyohimban-16a-carboxylic acid methyl ester hydrochloride (yohimbine hydrochloride), 2-[(2,3-dihydro-1,4-benzodioxin-2-yl)methyl]-1-ethyl-1H-imidazole, and combinations and pharmaceutically acceptable salts thereof.

In a further embodiment, said adrenergic$_{\alpha 2}$ receptor antagonist is an adrenergic$_{\alpha 2B}$ receptor antagonist selected from a group consisting of 2-(1-ethyl-2-imidazoyl)methyl-1,4-benzodioxan (imiloxan), 2-[(2,3-dihydro-1,4-benzodioxin-2-yl)methyl]-1-ethyl-1 H-imidazole, 2-[2-[4-(2-methoxyphenyl)-1- piperazinyl]ethyl]-4,4-dimethyl-1,3 (2H, 4H)-isoquinolinedione (ARC 239), or a combination or a pharmaceutical salt thereof.

The term "NET/SERT mediated conditions" or "NET and/or SERT mediated conditions" or "disease characterized by malregulation of NET/SERT" referred herein include but are not limited to one or more of the following diseases or conditions: dysphoria, depression (including major depressive disorder, dysthymia, adjustment disorder with depressed mood, and depression associated with bipolar disorder), anxiety, sleep disorders, gastric motility disorders, sexual dysfunction, brain trauma, memory loss, appetite disorders, bulimia, obesity, substance abuse, alcoholism, tobacco addiction, obsessive-compulsive disease, panic disorder, premenstrual syndrome, migraine, bipolar disorders, neuropathic pain (e.g., chronic pain, e.g., fibromyalgia), attention deficit hyperactive disorder (ADHD), Alzheimer's Disease and naturally, surgically or medically induced menopausal or andropausal symptoms such as vasomotor symptoms, e.g., hot flashes. Therefore, the methods of the disclosure encompass methods of treating these diseases. In a preferred embodiment, the disease or condition of the methods of the disclosure is depression or anxiety. In another preferred embodiment the disease or condition of the method of the disclosure is vasomotor symptoms, e.g., hot flashes.

The term "subject" includes a warm-blooded animal, including the human species and intends to include both the male or female gender unless otherwise indicated. The subject according to the current disclosure for the treatment of vasomotor symptoms, e.g., hot flashes includes not only women of advanced age who have gone through menopause (postmenopausal), but also pre- or peri-menopausal female wherein menopause may be naturally, chemically and/or surgically induced (e.g., those who have undergone oophorectomy, hysterectomy, chemotherapy, radiation of the pelvis or those who have suppressed estrogen production such as those who have undergone long-term use of corticosteroids or suffer from Cushing's syndrome or gonadal dysgenesis). The term subject according to the current disclosure for the treatment of vasomotor symptoms, e.g., hot flashes also includes andropausal male.

The term "pre-menopausal" or "premature menopause" means before the menopause. Both "premature menopause" and "artificial menopause" may refer to menopause that occurs as a result of, e.g., ovarian failure of unknown cause that may occur before age of 40. It may also be associated with smoking, living at high altitude, or poor nutritional status. Artificial menopause may result from oophorectomy, chemotherapy, radiation of the pelvis, or any process that impairs ovarian blood supply.

The term "peri-menopausal" means during the menopause.

The term "post-menopausal" means after the menopause.

The term "andropause" refers to condition or disorder characterized by symptoms, including, but not limited to reduction in Leydig cell numbers and a decline in androgen production, occurring in men, generally after middle age. Andropausal men therefore may also experience symptoms including, but not limited to fatigue, insomnia, hot flushes, and sweating. Accordingly, the current disclosure also anticipates use of the compounds of the present disclosure by naturally, chemically and/or surgically induced andropausal male.

In the above, other pharmaceutical composition, process, method, use and medicament manufacture features, the alternative and preferred embodiments of the compounds of the disclosure described herein also apply.

METHODS OF MAKING THE COMPOUNDS OF THE DISCLOSURE

The disclosure will now be illustrated by the following non limiting examples in which, unless stated otherwise.

The compounds of the disclosure may be made following the reaction route outlined in Scheme 1 below:

Scheme I

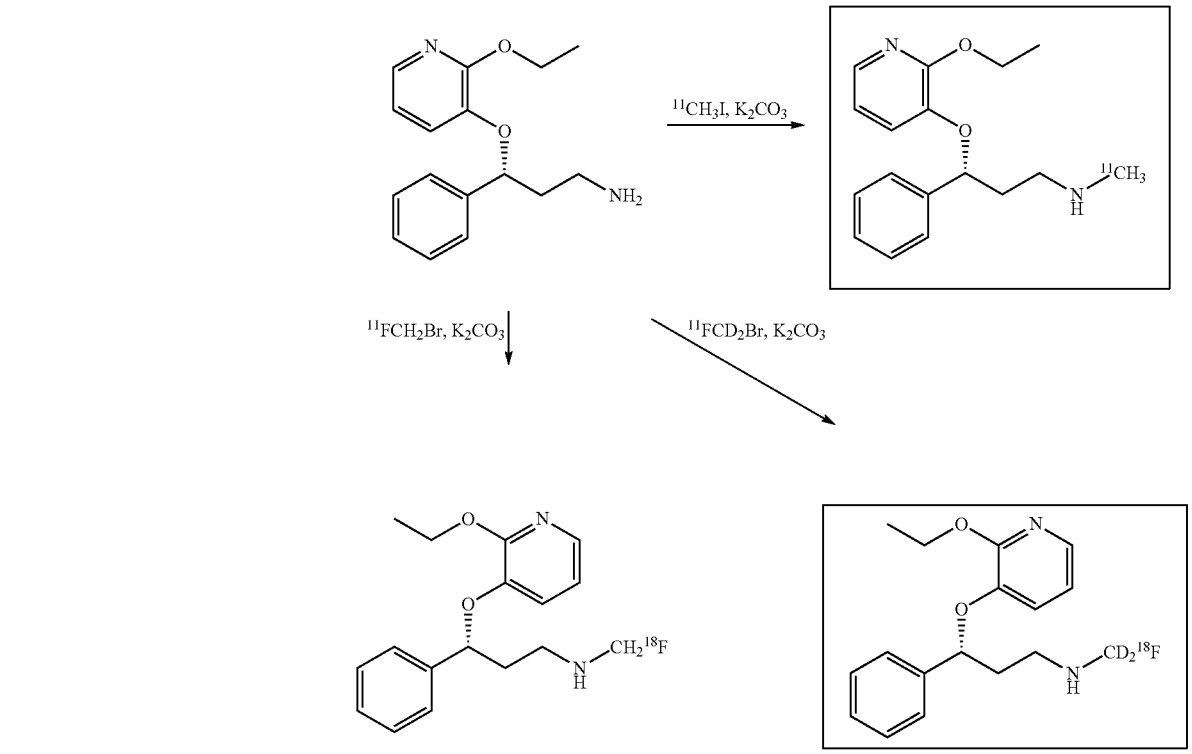

The conditions and reagents for the steps are as follows: (a) PPh$_3$, diisopropyl azodicarboxylate, 0° C.; (b) C$_{1-4}$alkylamine (e.g., 40% aqueous methylamine) or 28% ammonium hydroxide, microwaved in sealed reactor to 80°-90° C. for about 2-4 h; (c) di-tert-butyl dicarbonate, DIPEA, DMAP; (d) alkane diol (e.g., ethan-1,2-diol) and copper iodide, or sodium alkoxide (e.g., sodium methoxide), microwaved in seal reactor to about 150° C. for 1 hour; (e) acid (e.g., trifluoroacetic acid).

For a particular stereoconformation, the compounds may also be made by starting with commercially available optically pure (S)-(−)-3-chloro-1-phenylpropan-1-ol, utilizing mild Mitsunobu reaction conditions, condensed with substituted pyridinols in the presence of diisopropanyl azodicarboxylate (DIAD) and triphenyl phosphine (TPP) (O. Mitsunobu, Synthesis, 1-30(1981)). The reactions will result in complete inversion of the chiral benzylic carbon to give the corresponding chiral (R)-chloro compounds (K. Yasushi et al., Nucl. Med. Biol, 3 L: 147-153(2004)). Treatment of chloro compounds with excess 40% aqueous methylamine in ethyl alcohol or 28% ammonium hydroxide at 80°-90° C. using microwave under sealed flask to afford amine or methyl amine compounds. Similarly, the (S) enantiomer of the compounds above may be prepared using the (R)-(−)-3-chloro-1-phenylpropan-1-ol starting material in the Mitsunobu reaction as discussed herein.

The NET/SERT tracer compounds of the disclosure may be prepared according to the procedure as described in the following:

Example 1

(R)-2-(3-(3-(Methylamino)-1-phenylpropoxy)pyridin-2-yloxy)ethanol

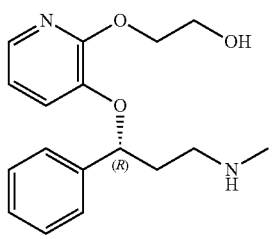

Step (a) (R)-3-(3-Chloro-1-phenylpropoxy)-2-iodopyridine: To a solution of (S)-3-chloro-1-phenylpropan-1-ol (5.11 g, 0.030 mol) in anhydrous THF (60 mL) is added PPh$_3$ (8.0 g, 0.031 mol). The mixture is stirred at room temperature for 10 min, and then cooled to 0° C. in an ice bath. 2-Iodopyridin-3-ol (7.0 g, 0.031 mol) is added into the reaction mixture, followed by adding diisopropyl azodicarboxylate (9.4 mL, 0.047 mol) dropwise over 10 min. The mixture is stirred at room temperature overnight, and then diluted with ethyl acetate (300 mL), followed by washing successively with saturated NaHCO$_3$ aqueous solution and brine. The organic phase is evaporated to dryness and the obtained residue is purified by silica gel column chromatography to give (R)-3-(3-chloro-1-phenylpropoxy)-2-iodopyridine as an oil (9.11 g, 78% yield). MS (ESI) m/z 374.0 [M+H]$^+$.

Step (b) (R)-tert-Butyl 3-(2-iodopyridin-3-yloxy)-3-phenylpropyl(methyl)-carbamate: To a solution of (R)-3-(3-chloro-1-phenylpropoxy)-2-iodopyridine (4.49 g, 0.012 mol) in ethanol (2 mL) is added 40% methylamine aqueous solution (4 mL). The mixture is sealed in a microwave vial, and then heated in a microwave reactor at 80° C. for 4 hours. After solvents are removed under reduced pressure, the residue is further dried under vacuum to give (R)-3-(2-iodopyridin-3-yloxy)-N-methyl-3-phenylpropan-1-amine as a yellowish solid. This crude intermediate and di-tert-butyl dicarbonate (3.9 g, 0.018 mol) are dissolved in DMF (20 mL), followed by adding diisopropylethylamine (2 mL) and a catalytic amount of 4-dimethylaminopyridine. The mixture is stirred at room temperature for an hour, and then evaporated to dryness. The residue is treated with methylene chloride, and then washed successively with saturated NaHCO$_3$ aqueous solution and brine. The organic phase is evaporated to dryness and the obtained residue is purified by silica gel column chromatography eluting with hexanes and ethyl acetate to give (R)-tert-butyl 3-(2-iodopyridin-3-yloxy)-3-phenylpropyl(methyl)carbamate as a clear oil (2.8 g, 50% yield). MS (ESI) m/z 469.1 [M+H]$^+$.

Step (c) (R)-tert-Butyl 3-(2-(2-hydroxyethoxy)pyridin-3-yloxy)-3-phenylpropyl(methyl)carbamate: A mixture of (R)-tert-butyl 3-(2-iodopyridin-3-yloxy)-3-phenylpropyl(methyl)carbamate (310 mg, 0.66 mmol), copper iodide (6 mg) and 1,10-phenanthroline (11 mg) in ethane-1,2-diol (10 mL) in a sealed microwave vial is heated in a microwave reactor at 150° C. for an hour. The reaction mixture is cooled to room temperature, and then di-tert-butyl dicarbonate (57 mg, 0.26 mmol) is added. The mixture is stirred at room temperature for 30 min, and then treated with saturated NaHCO$_3$ aqueous solution. The mixture is extracted with ethyl acetate and the combined organic phase is evaporated to dryness. The obtained crude product is purified with a basic alumina column using a gradient of 0-100% ethyl acetate in hexanes over 30 min to give (R)-tert-butyl 3-(2-(2-hydroxyethoxy)pyridin-3-yloxy)-3-phenylpropyl (methyl)carbamate as a dense oil (239 mg, 90% yield). MS (ESI) m/z 403.3 [M+H]$^+$.

Step (d) (R)-2-(3-(3-(Methylamino)-1-phenylpropoxy)pyridin-2-yloxy)ethanol: To a solution of (R)-tert-butyl 3-(2-(2-hydroxyethoxy)pyridin-3-yloxy)-3-phenylpropyl (methyl)carbamate (22 mg, 0.055 mmol) in methylene chloride (1 mL) is added trifluoroacetic acid (0.5 mL). The reaction mixture is stirred at room temperature for an hour, and then evaporated to dryness under reduced pressure. The residue is purified with a semi-preparative HPLC using a gradient of 0-25% acetonitrile in water containing 0.1% formic acid over 16 min to give (R)-2-(3-(3-(methylamino)-1-phenylpropoxy)pyridin-2-yloxy)ethanol as a clear oil (16 mg, 96% yield). MS (ESI) m/z 303.2 [M+H]$^+$.

Example 2

(R)-3-Phenyl-3-(2-ethoxypyridin-3-yloxy)propan-1-amine

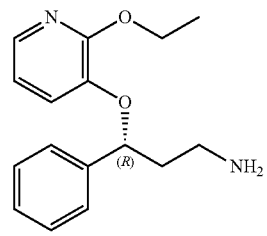

Step (a) (R)-3-(3-Chloro-1-phenylpropoxy)-2-ethoxypyridine: To a solution of (S)-3-chloro-1-phenylpropan-1-ol (0.82 g, 4.8 mmol) in anhydrous THF (10 mL) is added PPh$_3$ (1.26 g, 4.8 mmol). The mixture is stirred at room temperature for 10 min, and then cooled to 0° C. 2-Ethoxypyridin-3-ol (0.67 g, 4.8 mmol) is added into the reaction mixture, followed by adding 40 wt. % diethyl azodicarboxylate in toluene (3.0 mL, 6.6 mmol) dropwise. The reaction mixture is stirred at room temperature overnight, and then concentrated under reduced pressure. The obtained residue is purified by silica gel column chromatography to give (R)-3-(3-chloro-1-phenylpropoxy)-2-ethoxypyridine as a yellowish oil (1.06 g, 76% yield). MS (ESI) m/z 292.1 [M+H]$^+$.

Step (b) (R)-3-(2-Ethoxypyridin-3-yloxy)-3-phenylpropan-1-amine: To a solution of (R)-3-(3-chloro-1-phenylpropoxy)-2-ethoxypyridine (160 mg, 0.55 mmol) in ethanol (1 mL) is added 28% ammonium hydroxide aqueous solution (2 mL). The mixture is sealed in a microwave vial, and then heated in a microwave reactor at 90° C. for two hours. The reaction mixture is cooled to room temperature and then evaporated under reduced pressure. The obtained residue is purified with a semi-preparative HPLC using a gradient of 0-35% acetonitrile in water containing 0.1% formic acid over 16 min to give (R)-3-(2-ethoxypyridin-3-yloxy)-3-phenylpropan-1-amine as an off-white solid (130 mg, 87% yield). $^1$H NMR (500 MHz, Chloroform-d) δ 8.52 (br, 4H), 7.71 (dd, J=5.0, 1.5 Hz, 1H), 7.41-7.28 (m, 5H), 6.69 (dd, J=7.8, 1.6 Hz, 1H), 6.59 (dd, J=7.8, 5.0 Hz, 1H), 5.18 (dd, J=9.1, 3.6 Hz, 1H), 4.56-4.39 (m, 2H), 3.39-3.24 (m, 1H), 3.24-3.12 (m, 1H), 2.47-2.33 (m, 1H), 2.30-2.19 (m, 1H), 1.48 (t, J=7.1 Hz, 3H). $^{13}$C NMR (126 MHz, Chloroform-d)

δ 154.8, 141.5, 139.6, 139.0, 129.0, 128.5, 125.8, 123.0, 116.6, 82.1, 62.2, 37.6, 35.6, 14.6. MS (ESI) m/z 273.2 [M+H]⁺.

Example 3

(R)-3-(2-Ethoxypyridin-3-yloxy)-N-methyl-3-phenylpropan-1-amine

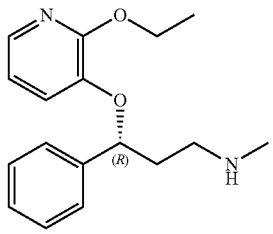

To a solution of (R)-3-(3-chloro-1-phenylpropoxy)-2-ethoxypyridine (1.3 g, 4.4 mmol) in ethanol (8 mL) is added 40% methylamine aqueous solution (4 mL). The mixture is sealed in a microwave vial, and then heated in a microwave reactor at 85° C. for two hours. The reaction mixture is cooled to room temperature and then evaporated to dryness under reduced pressure. The obtained residue is purified with a semi-preparative HPLC using a gradient of 0-35% acetonitrile in water containing 0.1% formic acid over 16 min to give (R)-3-(2-ethoxypyridin-3-yloxy)-N-methyl-3-phenylpropan-1-amine as a clear thick oil (880 mg, 70% yield). ¹H NMR (500 MHz, Chloroform-d) δ 8.56 (s, 1H), 7.71 (dd, J=5.0, 1.6 Hz, 1H), 7.41-7.28 (m, 5H), 6.73 (dd, J=7.8, 1.6 Hz, 1H), 6.61 (dd, J=7.8, 5.0 Hz, 1H), 5.24-5.18 (m, 1H), 4.49 (q, J=7.2 Hz, 2H), 3.31-3.11 (m, 2H), 2.71 (s, 3H), 2.47-2.35 (m, 1H), 2.35-2.23 (m, 1H), 1.48 (t, J=7.1 Hz, 3H). ¹³C NMR (126 MHz, Chloroform-d) δ 155.1, 141.6, 139.4, 138.7, 129.0, 128.5, 125.8, 123.0, 116.8, 80.2, 53.7, 46.6, 34.3, 32.9. MS (ESI) m/z 287.2 [M+H]⁺.

Example 4

(R)-N-ethyl-3-(2-methoxypyridin-3-yloxy)-3-phenylpropan-1-amine

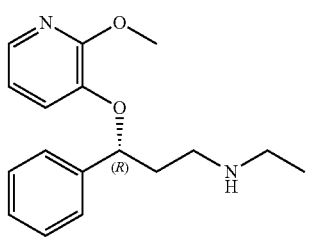

Step (a) (R)-3-(3-Chloro-1-phenylpropoxy)-2-iodopyridine: To a solution of (S)-3-chloro-1-phenylpropan-1-ol (5.11 g, 0.030 mol) in anhydrous THF (60 mL) is added PPh₃ (8.0 g, 0.031 mol). The mixture is stirred at room temperature for 10 min, and then cooled to 0° C. in an ice bath. 2-Iodopyridin-3-ol (7.0 g, 0.031 mol) is added into the reaction mixture, followed by adding diisopropyl azodicarboxylate (9.4 mL, 0.047 mol) dropwise over 10 min. The mixture is stirred at room temperature overnight, and then diluted with ethyl acetate (300 mL), followed by washing successively with saturated NaHCO₃ aqueous solution and brine. The organic phase is evaporated to dryness and the obtained residue is purified by silica gel column chromatography eluting with 20% ethyl acetate in hexanes to give (R)-3-(3-chloro-1-phenylpropoxy)-2-iodopyridine as an oil (9.11 g, 78% yield). MS (ESI) m/z 374.0 [M+H]⁺.

Step (b) (R)-N-ethyl-3-(2-iodopyridin-3-yloxy)-3-phenylpropan-1-amine: To a solution of (R)-3-(3-chloro-1-phenylpropoxy)-2-iodopyridine (45 mg, 0.12 mmol) in ethanol (0.3 mL) is added 70% ethylamine aqueous solution (0.3 mL). The mixture is sealed in a microwave vial, and then heated in a microwave reactor at 80° C. for two hours. The reaction mixture is cooled to room temperature and then evaporated to dryness under reduced pressure. The obtained residue is purified using a semi-preparative HPLC equipped a reverse phase C18 column eluting with a gradient of 0% to 20% acetonitrile in water containing 0.1% formic acid to give (R)-N-ethyl-3-(2-iodopyridin-3-yloxy)-3-phenylpropan-1-amine as a clear thick oil (30 mg, 65% yield). MS (ESI) m/z 383.1 [M+H]⁺.

Step (c) (R)-N-ethyl-3-(2-methoxypyridin-3-yloxy)-3-phenylpropan-1-amine: A mixture of (R)-N-ethyl-3-(2-iodopyridin-3-yloxy)-3-phenylpropan-1-amine (30 mg, 0.078 mmol) and CuI (15 mg, 0.079 mmol) in 5M sodium methoxide in methanol (0.9 mL) in a sealed microwave vial is heated in a microwave reactor at 100° C. for two hours. The reaction mixture is cooled to room temperature and then diluted with 10 mL of water, followed by extractions with CH₂Cl₂ (3×15 mL). The combined organic phase is evaporated to dryness. The obtained crude product is purified using a semi-preparative HPLC equipped a reverse phase C18 column eluting with a gradient of 0% to 20% acetonitrile in water containing 0.1% formic acid to give (R)-N-ethyl-3-(2-methoxypyridin-3-yloxy)-3-phenylpropan-1-amine as an oil (11.2 mg, 50% yield). ¹H NMR (500 MHz, Chloroform-d) δ 9.53 (br, 2H), 7.71 (dd, J=5.0, 1.4 Hz, 1H), 7.38-7.24 (m, 5H), 6.75 (dd, J=7.8, 1.5 Hz, 1H), 6.62 (dd, J=7.8, 5.0 Hz, 1H), 5.23 (dd, J=8.7, 3.6 Hz, 1H), 4.03 (s, 3H), 3.27-3.10 (m, 2H), 3.10-2.92 (m, 2H), 2.50-2.35 (m, 1H), 2.35-2.22 (m, 1H), 1.32 (t, J=7.2 Hz, 3H). MS (ESI) m/z 387.2 [M+H]⁺.

Example 5

(R)-3-(2-ethoxypyridin-3-yloxy)-N-ethyl-3-phenylpropan-1-amine

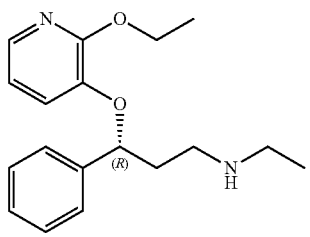

The compound is synthesized using a method similar to the one described in Example 4 except that 5M sodium ethoxide in methanol is used in step (c) instead of 5M sodium methoxide in methanol. ¹H NMR (500 MHz, Chloroform-d) δ 9.42 (br, 2H), 7.69 (dd, J=5.0, 1.5 Hz, 1H), 7.39-7.21 (m, 5H), 6.77 (dd, J=7.8, 1.6 Hz, 1H), 6.59 (dd, J=7.8, 4.9 Hz, 1H), 5.20 (dd, J=8.8, 3.8 Hz, 1H), 4.47 (q, J=7.0 Hz, 2H), 3.15 (t, J =6.6 Hz, 2H), 3.08-2.88 (m, 2H), 2.51-2.33 (m, 1H), 2.33-2.19 (m, 1H), 1.45 (t, J=7.0 Hz, 3H), 1.28 (t, J=7.2 Hz, 3H). MS (ESI) m/z 301.2 [M+H]⁺.

Biology

The NET and SERT binding may be assayed to determine if the compounds of the disclosure specifically bind to NET or SERT. An exemplary procedure for assaying NET binding may be found in Raisman et al., *Eur. Jrnl. Pharmacol.* (1982) 78:345-351 and in Langer et al., *Eur. Jrnl. Pharmac.* (1981) 72:423. An exemplary procedure for assaying SERT binding may be found in D'Amato et al., *Jrnl. Pharmcacol. & Exp. Ther.* (1987) 242:364-371 and in Brown et al., *Eur. Jrnl. Pharmac.* (1986) 123:161-165. The contents of each of these references are incorporated by reference in their entirety.

The binding affinity of the compounds of the current disclosure is measured using a Novascreen against rodent NET, human NET and human SERT. Duloxetine is used as a positive control. Details of the Novascreen may be found in the following:

http://www.perkinelmer.com/Catalog/Product/ID/100-0123,
http://www.perkinelmer.com/Catalog/Product/ID/100-0048,
http://www.perkinelmer.com/Catalog/Product/ID/100-0146, and
http://www.perkinelmer.com/Catalog/Product/ID/100-0099.

For the binding affinity of the compounds of the current disclosure against NET, the following paramenters are used:
Assay Type: Binding
Species: Rat
Origin: Forebrain
Ligand: [3H]-Nisoxetine
Ligand [M]: 1.00E-09
Kd (Binding Affinity): 9.00E-10
Bmax: 10.5 fmol/mg tissue (wet weight)
Method: Radioactivity
Measurement: DPM
Assay Name: Norepinephrine, Transporter NET (h)
Assay Type: Binding
Species: Human
Origin: Recombinant/CHO cells
Ligand: [3H]-Nisoxetine
Ligand [M]: 1.00E-09
Kd (Binding Affinity): 3.00E-09
Bmax: 10 pmol/mg protein
Method: Radioactivity
Measurement: DPM For the binding affinity of the compounds of the current disclosure for SERT, the following paramenters are used:
Assay Name: Serotonin, Transporter SERT (h)
Assay Type: Binding
Species: Human
Origin: Platelets
Ligand: [3H]Citalopram, N-Methyl
Ligand [M]: 7.00E-10
Kd (Binding Affinity): 2.50E-09
Bmax: 425 fmol/mg protein
Method: Radioactivity
Measurement: DPM Using the Novascreen as described or similarly described above, the compounds of the present disclosure show the following binding affinities:

| Example | NET, ($K_i$ nM) | NET(h), ($K_i$ nM) | SERT (h), ($K_i$ nM) |
| --- | --- | --- | --- |
| Example 1 | N/A | 39 | N/A |
| Example 2 | N/A | 69 | N/A |
| Example 3 | N/A | 4.20 | 318 |
| Compound 4 | N/A | 81.4 | 240 |
| Compound 5 | N/A | 37.3 | 579 |
| Compound of claim 2* of WO 2008/150528 | 23.2 | 13.0 | 26.4 |
| Example 16 of WO 2008/150528 | 14.8 | 11.7 | 55.2 |
| Example 6 of WO 2008/150528 | 46.8 | 43.5 | 56.9 |
| Example 21 of WO 2008/150528 | N/A | 16.1 | 39.3 |

*the compound of Formula (I) of WO 2008/150528, wherein Y is N; X is CH and Z is C(R), wherein R is I and n is 1 and R is methyl.

Effects of the Compounds of the Disclosure on Vasomotor Symptoms

Overiectomized Rat Model: The effectiveness of the compounds of the present disclosure to reduce hot flashes may be evaluated according to the procedure provided in Maswood et. al., Neuroendocrinology 84:330-338 (2006). Ovariectomized female rats may be housed on a 12-hour light/dark cycle. A telemetric transmitter may be implanted in the dorsal scapular region of the rat and tip of the tunnel probe is inserted 2.5 cm beyond the base of the tail to measure the tail skin temperature (TST). For measurement of the core body temperature (CBT), a 3-4 cm long incision may be made in the midline of the abdomen of the rats through the abdominal musculature and a transmitter is placed in the abdominal cavity. A vehicle may be administered subcutaneously to the rat 0.5 h before the onset of the dark phase and TST is monitored continuously for 12 hours to establish the baseline. Twenty-four hours later, either vehicle or test compounds of the present disclosure may be administered subcutaneously. TST may be monitored for 12 hours. An average temperature may be calculated for every 30-min time point. The change in temperature may be calculated by taking the average temperature for each 30-min time point on the compound dosing day minus the overall average baseline temperature on vehicle dosing day (average temperature over 12 hours).

Morphine-dependent Rat Model: The effectiveness of the compounds of the present disclosure to reduce hot flashes may be evaluated by measuring its ability to reduce morphine-induced rise in TST. Ovariectomized rats may be subcutaneously injected with a vehicle (sterile water) once daily for 8 days. On day-4, two tablets of slow-release morphine may be implanted subcutaneously in the dorsal scapular region of the rats to induce morphine dependence. On day-5 and -6, morphine withdrawal may be induced by subcutaneous administration of 1.0 mg/Kg of naloxone, a general opioid antagonist. Compounds of the present disclosure or combinations thereof may be administered (1.0, 5, 10, 20, 40 mg/Kg) to the rats 1 hour before naloxone injection. Ketamine (40 mg/Kg) may be injected after test compound to induce sedation so as to avoid temperature fluctuation due to stress associated with restriction of their movement and attachment of thermistor probe to the their tails. All drug- related effects may be compared to a vehicle control group which also receives ketamine. TST may be monitored continuously for 35 minutes. The average TST measured 25, 30 and 35 minutes prior to naloxone injection may be used to establish a baseline temperature. Hot flash reduction may be determined by evaluating the statistical differences between the baseline temperature and 15 minutes after naloxone treatment when the change in TST may be observed to be maximum.

Using the morphine-dependent rat model as described or similarly described, the compound of Example 3 at 30 mg/kg p.o. is tested and shows to be effective in reducing naloxone-induced flush. The results are shown in FIG. 1.

The invention claimed is:

1. A compound of Formula I:

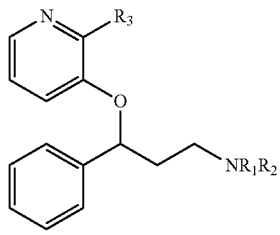

in free or salt form, wherein:
$R_1$ and $R_2$ are independently H or $C_{1-4}$ alkyl; and
$R_3$ is —O—$C_{2-4}$ alkyl optionally substituted with hydroxy.

2. The compound according to claim 1, selected from a group of the following:

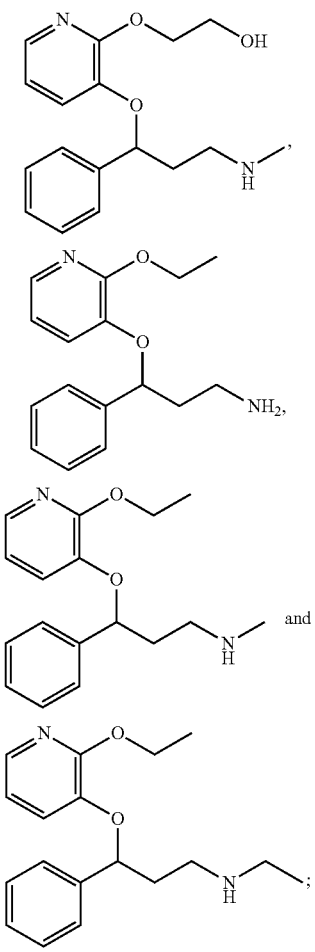

in free or salt form.

3. The compound according to claim 1, selected from a group of the following:

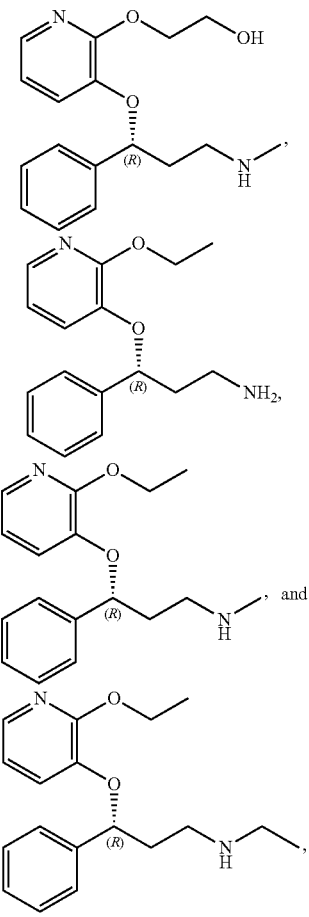

in free or salt form.

4. The compound according to claim 1, wherein said compound is enriched with the (R) enantiomer in greater than 60% enantiomeric excess.

5. The compound according to claim 1, wherein said compound is enriched with the (S) enantiomer in greater than 60% enantiomeric excess.

6. The compound according to claim 1, wherein $R_3$ is ethoxy or hydroxy ethoxy.

7. The compound according to claim 1, wherein the compound is

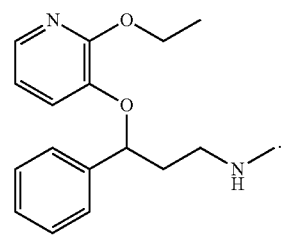 [SMILES: CCOc1ncccc1OC(CCNC)c1ccccc1]

8. A NET/SERT tracer compound comprising a compound of claim 1 and a radionuclide chemically bound to the compound.

9. The NET/SERT tracer compound of claim 8, wherein the radionuclide is selected from Carbon-11, Fluorine-18, Technetium-99m, Indium-111, and Iodine-123.

10. The compound of claim 9, wherein the compound is selected from

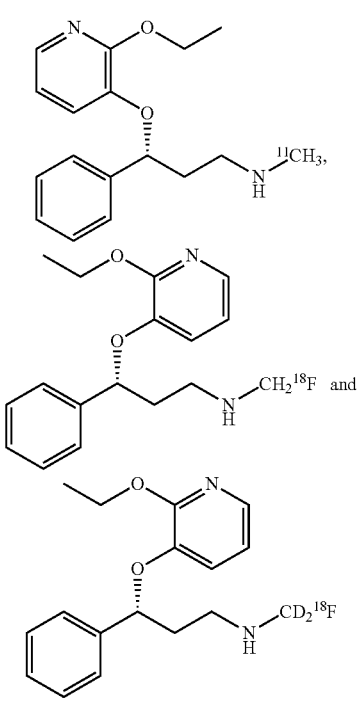

in free or salt form.

11. A pharmaceutical composition comprising the compound according to claim 1, in free or pharmaceutically acceptable salt form, in association with a pharmaceutically-acceptable diluent or carrier.

12. The pharmaceutical composition according to claim 11, further comprising an adrenergic$_{\alpha 2}$ receptor antagonist.

13. The pharmaceutical composition according to claim 12, wherein the adrenergic$_{\alpha 2}$ receptor antagonist is an adrenergic$_{\alpha 2B}$ receptor antagonist.

14. A method of treating a disease or condition mediated by NET/SERT comprising administering an effective amount of a compound according to claim 1, in free or pharmaceutically acceptable salt form wherein the disease or condition is selected from a group consisting of dysphoria, depression, anxiety, sleep disorders, gastric motility disorders, sexual dysfunction, brain trauma, memory loss, appetite disorders, bulimia, obesity, substance abuse, alcoholism, tobacco addiction, obsessive-compulsive disease, panic disorder, premenstrual syndrome, migraine, bipolar disorders, neuropathic pain, attention deficit hyperactive disorder (ADHD), Alzheimer's Disease, and vasomotor symptoms.

15. The method according to claim 14, wherein the disease or condition is depression.

16. The method according to claim 14, wherein the disease or condition is anxiety.

17. The method according to claim 14, wherein the vasomotor symptom is hot flashes.

18. The method of claim 14, further comprising administering an effective amount of an adrenergic$_{\alpha 2}$ receptor antagonist.

19. The method according to claim 18, wherein the adrenergic$_{\alpha 2}$ receptor antagonist is an adrenergic$_{\alpha 2B}$ receptor antagonist.

* * * * *